United States Patent [19]
Villhauer

[11] Patent Number: 6,166,063
[45] Date of Patent: Dec. 26, 2000

[54] N-(SUBSTITUTED GLYCYL)-2-CYANOPYRROLIDINES, PHARMACEUTICAL COMPOSITIONS CONTAINING THEM AND THEIR USE IN INHIBITING DIPEPTIDYL PEPTIDASE-IV

[75] Inventor: Edwin Bernard Villhauer, Morristown, N.J.

[73] Assignee: Novartis AG, Basel, Switzerland

[21] Appl. No.: 09/458,224

[22] Filed: Dec. 9, 1999

Related U.S. Application Data

[63] Continuation of application No. 09/209,068, Dec. 10, 1998, abandoned.

[51] Int. Cl.[7] .......................... A61K 31/401; A61P 5/48; C07D 207/12; C07D 207/14
[52] U.S. Cl. ......................... 514/423; 514/428; 548/528; 548/530
[58] Field of Search .................................. 514/423, 428; 548/530, 528

[56] References Cited

U.S. PATENT DOCUMENTS 4,661,512  4/1987  Laruelle et al. .................. 514/423

FOREIGN PATENT DOCUMENTS

| 555 824 A1 | 8/1993 | European Pat. Off. . |
| 1581 09 | 12/1982 | Germany . |
| 296 075 A5 | 11/1991 | Germany . |
| WO90/12005 | 10/1990 | WIPO . |
| WO91/16339 | 10/1991 | WIPO . |
| WO93/08259 | 4/1993 | WIPO . |
| WO95/11689 | 5/1995 | WIPO . |
| WO95/13069 | 5/1995 | WIPO . |
| WO95/15309 | 6/1995 | WIPO . |
| WO95/29190 | 11/1995 | WIPO . |
| WO95/29691 | 11/1995 | WIPO . |
| WO95/34538 | 12/1995 | WIPO . |
| WO98/19998 | 5/1998 | WIPO . |
| WO99/38501 | 8/1999 | WIPO . |

OTHER PUBLICATIONS

Li, et al. Archives of Biochemistry and Biophysics, vol. 323, No. 1, pp. 148–154 (1995).

Li, et al. Journal of Neurochemistry, vol. 66, pp. 2105–2112 (1996).

Yamada, et al. Bulletin of the Chemical Society of Japan, vol. 50, No. 7, pp. 1827–1830 (1977).

Yamada, et al. Bulletin of the Chemical Society of Japan, vol. 51, No. 3, pp. 878–883 (1978).

Derwent Abstract 95: 302548. (1994).

Derwent Abstract 84: 177689. (1983).

Derwent Abstract 96: 116353. (1994).

Kaspari, et al. Biochimica et Biophysica, vol. 1293, pp. 147–153 (1996).

Ashworth, et al. Bioorganic and Medicinal Chemistry Letters, vol. 6, No. 10, pp. 1163–1166 (1996).

Coutts, et al. J. Med Chem., vol. 39, pp. 2087–2094 (1996).

Deacon, et al. Diabetes, vol. 44, pp. 1126–1131 (Sep. '96).

Ashworth, et al. Bioorganic and Medicinal Chemistry Letters, vol. 6, No. 22, pp. 2745–2748 (1996).

Augustyns, et al. Eur J. Med. Chem., vol. 32, pp. 301–309 (1997).

Hughes, et al. Biochemistry, vol. 38, pp. 11597–11603 (1999).

Primary Examiner—Robert W. Ramsuer
Assistant Examiner—Jane C. Oswecki
Attorney, Agent, or Firm—Joseph J. Borovian

[57] ABSTRACT

The present invention relates to a compound of formula (I)

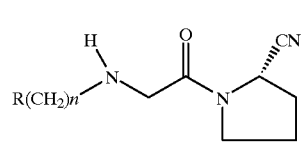

wherein R is substituted adamantyl; and n is 0 to 3; in free form or in acid addition salt form. Compounds of formula I inhibit DPP-IV (dipeptidyl-peptidase-IV) activity. They are therefore indicated for use as pharmaceuticals in inhibiting DPP-IV and in the treatment of conditions mediated by DPP-IV, such as non-insulin-dependent diabetes mellitus, arthritis, obesity, osteoporosis and further conditions of impaired glucose tolerance.

9 Claims, No Drawings

N-(SUBSTITUTED GLYCYL)-2-CYANOPYRROLIDINES, PHARMACEUTICAL COMPOSITIONS CONTAINING THEM AND THEIR USE IN INHIBITING DIPEPTIDYL PEPTIDASE-IV

This application claims the benefit of U.S. application Ser. No. 09/209,068, filed Dec. 10, 1998, now abandoned, and which is incorporated herein by reference.

The present invention provides new dipeptidyl peptidase-IV (DPP-IV) inhibitors which are effective in treating conditions mediated by DPP-IV. More recently, it was discovered that DPP-IV is responsible for inactivating glucagon-like peptide-1 (GLP-1). Since GLP-1 is a major stimulator of pancreatic insulin secretion and has direct beneficial effects on glucose disposal, DPP-IV inhibition appears to represent an attractive approach for treating conditions such as non-insulin-dependent diabetes mellitus (NIDDM).

The instant invention relates to novel N-(substituted glycyl)-2-cyanopyrrolidines of formula I:

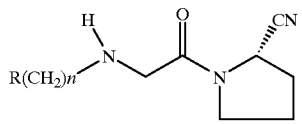

wherein
R is substituted adamantyl; and
n is 0 to 3; in free form or in acid addition salt form.

The compounds of formula I can exist in free form or in acid addition salt form. Pharmaceutically acceptable (i.e., non-toxic, physiologically acceptable) salts are preferred, although other salts are also useful, e.g., in isolating or purifying the compounds of this invention. Although the preferred acid addition salts are the hydrochlorides, salts of methanesulfonic, sulfuric, phosphoric, citric, lactic and acetic acid may also be utilized.

The compounds of the invention may exist in the form of optically active isomers or diastereoisomers and can be separated and recovered by conventional techniques, such as chromatography.

Listed below are definitions of various terms used to describe this invention. These definitions apply to the terms as they are used throughout this specification, unless otherwise limited in specific instances, either individually or as part of a larger group.

The term "alkyl" refers to straight or branched chain hydrocarbon groups having 1 to 10 carbon atoms, preferably 1 to 7 carbon atoms, most preferably 1 to 5 carbon atoms. Exemplary alkyl groups include methyl, ethyl, propyl, isopropyl, n-butyl, t-butyl, isobutyl, pentyl, hexyl and the like.

The term "alkanoyl" refers to alkyl-C(O)—.

The term "substituted adamantyl" refers to adamantyl, i.e., 1- or 2-adamantyl, substituted by one or more, for example two, substitutents selected from alkyl, —$OR_1$ or —$NR_2R_3$; where $R_1$, $R_2$ and $R_3$ are independently hydrogen, alkyl, ($C_1$–$C_8$-alkanoyl), carbamyl, or —CO—$NR_4R_5$; where $R_4$ and $R_5$ are independently alkyl, unsubstituted or substituted aryl and where one of $R_4$ and $R_5$ additionally is hydrogen or $R_4$ and $R_5$ together represent $C_2$–$C_7$alkylene.

The term "aryl" preferably represents phenyl. Substituted phenyl preferably is phenyl substituted by one or more, e.g., two, substitutents selected from, e.g., alkyl, alkoxy, halogen and trifluoromethyl.

The term "alkoxy" refers to alkyl-O—.

The term "halogen" or "halo" refers to fluorine, chlorine, bromine and iodine.

The term "alkylene" refers to a straight chain bridge of 2 to 7 carbon atoms, preferably of 3 to 6 carbon atoms, most preferably 5 carbon atoms.

A preferred group of compounds of the invention is the compounds of formula I wherein the substituent on the adamantyl is bonded on a bridgehead or a methylene adjacent to a bridgehead. Compounds of formula I wherein the the glycyl-2-cyanopyrrolidine moiety is bonded to a bridgehead, the R' substituent on the adamantyl is preferably 3-hydroxy. Compounds of formula I wherein the the glycyl-2-cyanopyrrolidine moiety is bonded at a methylene adjacent to a bridgehead, the R' substituent on the adamantyl is preferably 5-hydroxy.

The present invention especially relates to a compound of formulae (I A) or (I B)

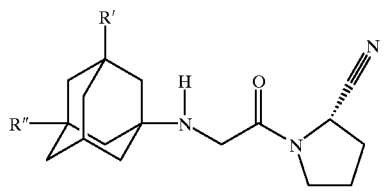

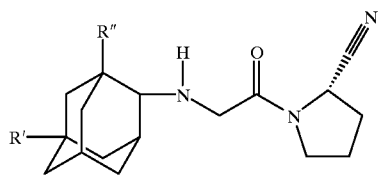

wherein R' represents hydroxy, $C_1$–$C_7$alkoxy, $C_1$–$C_8$-alkanoyloxy, or $R_5R_4N$—CO—O—, where $R_4$ and $R_5$ independently are $C_1$–$C_7$alkyl or phenyl which is unsubstituted or substituted by a substitutent selected from $C_1$–$C_7$alkyl, $C_1$–$C_7$alkoxy, halogen and trifluoromethyl and where $R_4$ additionally is hydrogen; or $R_4$ and $R_5$ together represent $C_3$–$C_6$alkylene; and R" represents hydrogen; or R' and R" independently represent $C_1$–$C_7$alkyl; in free form or in form of a pharmaceutically acceptable acid addition salt.

The compounds of the invention may be prepared e.g. by a process which comprises coupling a reactive (2-cyanopyrrolidino)carbonylmethylene compound with an appropriate substituted amine; more particularly, for the preparation of the compounds of formula I, it comprises reacting a compound of formula II.

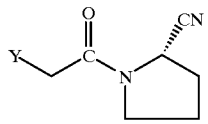

wherein Y is a reactive group (preferably a halogen such as bromine, chlorine or iodine) with a compound of formula III $$NH_2(CH_2)_n—R \qquad III$$

wherein R is as defined above, and recovering the resultant compound of formula I in free form or in acid addition salt form.

The process of the invention may be effected in conventional manner. For example, the compound of formula II is reacted with 1 to 3 equivalents, preferably 3 equivalents, of a primary amine of formula III. The reaction is conveniently conducted in the presence of an inert, organic solvent, such as methylene chloride or a cyclic ether such as tetrahydrofuran. The temperature preferably is of from about 0° to about 35° C., preferably between about 0° and about 25° C.

The compounds of the invention may be isolated from the reaction mixture and purified in conventional manner, e.g. by chromatography.

The starting materials may also be prepared in conventional manner. The compounds of formula II may be prepared by the following two-step reaction scheme:

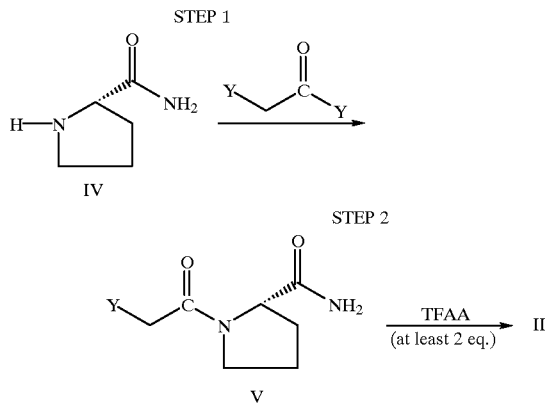

Step 1 involves the reaction of the pyrrolidine of formula IV with a slight molar excess of a haloacetylhalide such as bromoacetylbromide or chloroacetylchloride and a base such as potassium carbonate or triethylamine. The reaction conveniently is conducted in the presence of an inert, organic solvent, such as tetrahydrofuran or a chlorinated, aliphatic hydrocarbon such as methylene chloride, at a temperature of from about 0° to about 25° C., preferably at a temperature between about 0° and about 15° C.

Step 2 concerns the dehydration of the compound of formula V, prepared in Step 1, with 1 to 2 equivalents of trifluoroacetic anhydride (TFAA). The dehydration preferably is conducted in the presence of an inert, organic solvent such as tetrahydrofuran or a chlorinated, aliphatic hydrocarbon such as methylene chloride, at a temperature of from about 0° to about 25° C., preferably at a temperature between about 0° and about 15° C.

Insofar as its preparation is not particularly described herein, a compound used as starting material is known or may be prepared from known compounds in known manner or analogously to known methods or analogously to methods described in the Examples.

For example, the primary amine compounds of formula III are known and may be prepared by procedures documented in the literature, for example, Khim. -Farm. Zh. (1986), 20(7), 810–15.

Finally, compounds of the invention are either obtained in the free form, or as a salt thereof if salt forming groups are present.

Compounds of the invention having basic groups can be converted into acid addition salts, especially pharmaceutically acceptable acid addition salts. These are formed, for example, with inorganic acids, such as mineral acids, for example sulfuric acid, a phosphoric or hydrohalic acid, or with organic carboxylic acids. Preferred are salts formed with hydrochloric acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The instant invention also includes pharmaceutical compositions, for example, useful in inhibiting DPP-IV, comprising a pharmaceutically acceptable carrier or diluent and a therapeutically effective amount of a compound of formula I, or a pharmaceutically acceptable acid addition salt thereof.

In still another embodiment, the instant invention provides a method of inhibiting DPP-IV comprising administering to a mammal in need of such treatment a therapeutically effective amount of a compound of formula I, or a pharmaceutically acceptable acid addition salt thereof.

In a further embodiment, the instant invention provides a method of treating conditions mediated by DPP-IV inhibition comprising administering to a mammal in need of such treatment a therapeutically effective amount of a compound of formula I above, or a pharmaceutically acceptable acid addition salt thereof.

The present invention also relates to the use of a compound according to the instant invention or a pharmaceutically acceptable salt thereof, e.g., for the manufacture of a medicament for the prevention or treatment of diseases or conditions associated with elevated levels of DPP-IV.

As indicated above, all of the compounds of formula I, and their corresponding pharmaceutically acceptable acid addition salts, are useful in inhibiting DPP-IV. The ability of the compounds of formula I, and their corresponding pharmaceutically acceptable acid addition salts, to inhibit DPP-IV may be demonstrated employing the Caco-2 DPP-IV Assay which measures the ability of test compounds to inhibit DPP-IV activity from human colonic carcinoma cell extracts. The human colonic carcinoma cell line Caco-2 was obtained from the American Type Culture Collection (ATCC HTB 37). Differentiation of the cells to induce DPP-IV expression was accomplished as described by Reisher, et al. in an article entitled "Increased expression of intestinal cell line Caco-2" in Proc. Natl. Acad. Sci., Vol. 90, pgs. 5757–5761 (1993). Cell extract is prepared from cells solubilized in 10 mM Tris HCl, 0.15 M NaCl, 0.04 t.i.u. aprotinin, 0.5% nonidet-P40, pH 8.0, which is centrifuged at 35,000 g for 30 min. at 4° C. to remove cell debris. The assay is conducted by adding 20 μg solubilized Caco-2 protein, diluted to a final volume of 125 μl in assay buffer (25 mM Tris HCl pH 7.4, 140 mM NaCl, 10 mM KCl, 1% bovine serum albumin) to microtiter plate wells. After a 60 min. incubation at room temperature, the reaction is initiated by adding 25 μl of 1 mM substrate (H-Alanine-Proline-pNA; pNA is p-nitroaniline). The reaction is carried out at room temperature for 10 minutes after which time a 19 μl volume of 25% glacial acetic acid is added to stop the reaction. Test compounds are typically added as 30 μl additions and the assay buffer volume is reduced to 95 μl. A standard curve of free p-nitroaniline is generated using 0–500 μM solutions of free pNA in assay buffer. The curve generated is linear and is used for interpolation of substrate consumption (catalytic activity in nmoles substrate cleaved/min). The endpoint is determined by measuring absorbance at 405 nm in a Molecular Devices UV Max microtiter plate reader.

The potency of the test compounds as DPP-IV inhibitors, expressed as $IC_{50}$, is calculated from 8-point, dose-response curves using a 4-parameter logistic function.

The following IC$_{50}$ was obtained:

| Compound | Caco-2 DPP-IV (nM) |
|---|---|
| Ex. 1 | 3.5 ± 1.5 |
| Ex. 4 | 8 |

The ability of the compounds of formula I, and their corresponding pharmaceutically acceptable acid addition salts, to inhibit DPP-IV may also be demonstrated by measuring the effects of test compounds on DPP-IV activity in human and rat plasma employing a modified version of the assay described by Kubota, et al. in an article entitled "Involvement of dipeptidylpeptidase IV in an in vivo immune response" in Clin. Exp. Immunol., Vol. 89, pgs. 192–197 (1992). Briefly, 5 µl of plasma are added to 96-well flat-bottom microtiter plates (Falcon), followed by the addition of 5 µl of 80 mM MgCl$_2$ in incubation buffer (25 mMHEPES, 140 mM NaCl, 1% RIA-grade BSA, pH 7.8). After a 60 min. incubation at room temperature, the reaction is initiated by the addition of 10 µl of incubation buffer containing 0.1 mM substrate (H-Glycine-Proline-AMC;AMC is 7-amino-4-methylcoumarin). The plates are covered with aluminum foil (or kept in the dark) and incubated at room temperature for 20 min. After the 20 min. reaction, fluorescence is measured using a CytoFluor 2350 fluorimeter (Excitation 380 nm Emission 460 nm; sensitivity setting 4). Test compounds are typically added as 2 µl additions and the assay buffer volume is reduced to 13 µl. A fluorescence-concentration curve of free AMC is generated using 0–50 µM solutions of AMC in assay buffer. The curve generated is linear and is used for interpolation of substrate consumption (catalytic activity in nmoles substrate cleaved/min). As with the previous assay, the potency of the test compounds as DPP-IV inhibitors, expressed as IC$_{50}$, is calculated from 8-point, dose-response curves using a 4 parameter logistic function.

The following IC$_{50}$ was obtained:

| Compound | human plasma DPP-IV (nM) | rat plasma DPP-IV (nM) |
|---|---|---|
| Ex. 1 | 2.7 ± 0.1 | 2.3 ± 0.1 |
| Ex. 8 | 6 | 12 |

In view of their ability to inhibit DPP-IV, the compounds of formula I, and their corresponding pharmaceutically acceptable acid addition salts, are useful in treating conditions mediated by DPP-IV inhibition. Based on the above and findings in the literature, it is expected that the compounds disclosed herein are useful in the treatment of conditions such as non-insulin-dependent diabetes mellitus, arthritis, obesity, allograft transplantation and calcitonin-osteoporosis. In addition, based on the roles of glucagon-like peptides (such as GLP-1 and GLP-2) and their association with DPP-IV inhibition, it is expected that the compounds disclosed herein are useful for example, to produce a sedative or anxiolytic effect, or to attenuate post-surgical catabolic changes and hormonal responses to stress, or to reduce mortality and morbidity after myocardial infarction,or in the treatment of conditions related to the above effects which may be mediated by GLP-1 and/or GLP-2 levels.

More specifically, for example, the compounds of formula I, and their corresponding pharmaceutically acceptable acid addition salts, improve early insulin response to an oral glucose challenge and, therefore, are useful in treating non-insulin-dependent diabetes mellitus. The ability of the compounds of formula I, and their corresponding pharmaceutically acceptable acid addition salts, to improve early insulin response to an oral glucose challenge may be measured in insulin resistant rats according to the following method:

Male Sprague-Dawley rats that had been fed a high fat diet (saturated fat=57% calories) for 2–3 weeks were fasted for approximately 2 hours on the day of testing, divided into groups of 8–10, and dosed orally with 10 µmol/kg of the test compounds in CMC. An oral glucose bolus of 1 g/kg was administered 30 minutes after the test compound directly into the stomach of the test animals. Blood samples, obtained at various timepoints from chronic jugular vein catheters, were analyzed for plasma glucose and immunoreactive insulin (IRI) concentrations, and plasma DPP-IV activity. Plasma insulin levels were assayed by a double antibody radioimmunoassay (RIA) method using a specific anti-rat insulin antibody from Linco Research (St. Louis, Mo.). The RIA has a lower limit of detection of 0.5 µU/mL with intra- and inter-assay variations of less than 5%. Data are expressed as % increase of the mean of the control animals. Upon oral administration, each of the compounds tested amplified the early insulin response which led to an improvement in glucose tolerance in the insulin resistant test animals. The following results were obtained:

| Compound | Increase of Insulin Response at 10 µmol/kg |
|---|---|
| Ex. 1 | 64% |

The precise dosage of the compounds of formula I, and their corresponding pharmaceutically acceptable acid addition salts, to be employed for treating conditions mediated by DPP-IV inhibition depends upon several factors, including the host, the nature and the severity of the condition being treated, the mode of administration and the particular compound employed. However, in general, conditions mediated by DPP-IV inhibition are effectively treated when a compound of formula I, or a corresponding pharmaceutically acceptable acid addition salt, is administered enterally, e.g., orally, or parenterally, e.g., intravenously, preferably orally, at a daily dosage of 0.002–5, preferably 0.02–2.5 mg/kg body weight or, for most larger primates, a daily dosage of 0.1–250, preferably 1–100 mg. A typical oral dosage unit is 0.01–0.75 mg/kg, one to three times a day. Usually, a small dose is administered initially and the dosage is gradually increased until the optimal dosage for the host under treatment is determined. The upper limit of dosage is that imposed by side effects and can be determined by trial for the host being treated.

The compounds of formula I, and their corresponding pharmaceutically acceptable acid addition salts, may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intravenously, in the form of sterile injectable solutions or suspensions. The enteral and parenteral compositions may be prepared by conventional means.

The compounds of formula I, and their corresponding pharmaceutically acceptable acid addition salts, may be formulated into enteral and parenteral pharmaceutical compositions containing an amount of the active substance that is effective for treating conditions mediated by DPP-IV inhibition, such compositions in unit dosage form and such compositions comprising a pharmaceutically acceptable carrier.

The compounds of formula I (including those of each of the subscopes thereof and each of the examples) may be administered in enantiomerically pure form (e.g., ee >98%, preferably >99%) or together with the R enantiomer, e.g., in racemic form. The above dosage ranges are based on the compounds of formula I (excluding the amount of the R enantiomer).

The following examples show representative compounds encompassed by this invention and their synthesis. However, it should be clearly understood that they are for purposes of illustration only.

EXAMPLE 1

Pyrrolidine, 1-[(3-hydroxy-1-adamantyl)amino]acetyl-2-cyano-, (S)

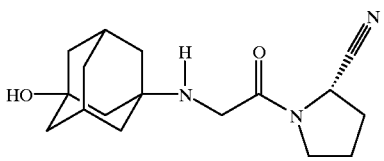

A. 1-Aminoadamantane-3-ol

Slight modifications to the synthesis found in Khim. -Farm. Zh. (1986), 20(7), 810–15, may be used.

To a rapidly stirred, clear and colorless, ice-water chilled mixture of concentrated sulfuric acid 96% (210 mL; 3,943 mmol) and 65% nitric acid (21.0 mL; 217.0 mmol) is added 21.0 g (112.0 mmol) of 1-adamantylamine HCl (99%), in small portions over 30 minutes. Upon adamantylamine hydrochloride addition, slight bubbling occurs and the reaction is slightly exothermic. This bubbling, yellow solution is stirred at ice-water temperature for about 2 hours and then at room temperature for 30 hours. This clear, light yellow reaction is then poured into about 100 g of ice and the resulting solution is clear green-blue.

The solution is placed in an ice-water bath and allowed to stir for 30 minutes. Approximately 550 g of 89% pure KOH (8.74 mol) is then added in small portions over 45 minutes. During this addition, the reaction is exothermic; reaching 80° C. and producing copious amounts of brown $NO_2$ gas. By the end of the addition, the reaction is thick with white solids (both product and salts). The resulting white paste is then poured onto a buchner funnel/celite pad and washed with 1.2 L of $CH_2Cl_2$. The $CH_2Cl_2$ layer is then extracted from the water layer and dried over $Na_2SO_4$. The solution is then filtered and concentrated (rotovap/pump) to provide 1-aminoadamantane-3-ol as a white solid.

Alternatively, the reaction may be carried out using n-butanol as solvent instead of methylene chloride.

Alternatively, 1-aminoadamantane-3-ol can be prepared e.g. as follows: A 2-L, 4-necked, round-bottomed flask is thoroughly flushed with nitrogen. The flask is charged under nitrogen with 420 mL of conc. sulfuric acid (98%). The contents are cooled to 8° C., then slowly (slightly exothermic & HCl gas evolution) 100.8 g of 1-aminoadamantane hydrochloride are added into the mixture in 8 portions at 9–10° C. over 20 min (minutes), then the hazy contents are stirred at 9–10° C. for 20 min to obtain a homogenous mixture. 72 mL of conc. (concentrated) nitric acid (70%) are added (very exothermic) dropwise into the mixture maintaining inner temperature at 14–15° C. with efficient cooling (at this scale 20 min. needed for this addition). The mixture is stirred at 14–15° C. for 20 min, the temperature is allowed to raise to 25° C. over 1 h (hour) (15–20° C. for 30 min, and 20–25° C. for 30 min), then the contents a stirred at 24–25.5° C. for 5 h (external cooling is needed). 1.7 L of water are charged into a 5-L, 4-necked flask, the water is cooled to 10° C., then the reaction mixture is slowly poured (very exothermic, some $NO_2$ gas evolution) over 25 min. maintaining the internal temperature below 35° C. to give a blue-green homogenous solution. The original 2-L flask (slightly exothermic) is rinsed once with 0.3 L of water and the water wash is poured into the 5-L flask. Slowly 900 mL of 50% sodium hydroxide aqueous solution are added (very exothermic, some $NO_2$ gas evolution) into the 5-L flask over 30 min. at 65–70° C. to bring the pH of the mixture to 13. 800 mL of 1-butanol and 200 mL of toluene are added (not exothermic) under vigorous stirring and allow the mixture to reach 30° C. The bottom aqueous layer is separated for proper disposal. The organic layer is once washed with 100 mL of saturated sodium chloride solution. The saturated sodium chloride wash is saved for disposal. The organic layer is concentrated at 60–85° C. (20–200 mbar) to give a pale yellow viscous oil. 600 mL of heptane and 50 mL of methanol are added into and the mixture is maintained at 40–50° C. for 15 min to give a thick suspension. The slurry is cooled to 12° C. and maintained at 12–14° C. for 15 min. The solids are filtered off through a polypropylene pad and Buchner funnel, then the flask and filter cake are washed once with 80 mL of heptane. The methanol/heptane filtrate is saved. The filter cake is dried at 55–60° C. (30 mbar) for 16 h to afford 1-aminoadamantane-3-ol as an off-white solid.

B. 1-Chloroacetyl-2-cyanopyrrolidine

To a mechanically stirred solution of 20.0 g (180.0 mmol) of chloroacetylchloride and 97 g (0.70 mmol) of potassium carbonate in 150 mL of tetrahydrofuran is added a solution of L-prolinamide 20.0 g (180.0 mmol) in 500 mL of tetrahydrofuran in a dropwise fashion over 45 minutes. This reaction is then mechanically stirred for an additional two hours at room temperature. The reaction is then filtered to remove potassium salts and the filtrate is dried over $Na_2SO_4$. The $Na_2SO_4$ is then removed via filtration and to this colorless filtrate is added trifluoroacetic anhydride (25.0 mL, 0.180 mmol) in one portion. The reaction is then magnetically stirred for 1 hour at room temperature and the resulting clear yellow/orange solution is concentrated via rotovap. The excess trifluoroacetic anhydride is removed by adding ethyl acetate to the concentrated oil and reconcentrating via rotovap. This removing operation is performed three times.

The resulting oil is partitioned between ethyl acetate and water. The product is then extracted into the ethyl acetate and the aqueous layer is then washed twice with ethyl acetate. The combined organic layers are then washed successively with water and brine dried over magnesium sulfate, filtered and concentrated to obtain 1-chloroacetyl-2-cyanopyrrolidine as a yellow solid.

Alternatively, the reaction may be carried out by using, as base, a mixture, e.g. 2-ethyl-hexanoic acid/sodium hydride.

C. Pyrrolidine, 1-[(3-hydroxy-1-adamantyl)amino]acetyl-2-cyano-, (S)

To a heterogeneous solution of the title A compound (1-aminoadamantane-3-ol (5.80 g, 34.7 mmol) in $CH_2Cl_2$ (68.0 mL) is added 9.6 g (69 mmol) of $K_2CO_3$. This heterogeneous mixture is then cooled in an ice-water bath and a solution of 3.0 g (17 mmol) of the title B compound (1-chloroacetyl-2-cyanopyrrolidine) dissolved in 25.0 mL of $CH_2Cl_2$ is added dropwise over a period of 30 minutes. The resulting mixture is stirred for 2 hours at 0° C. and at room temperature for 6 days. The reaction is then concentrated to obtain a yellow pasty material which is purified on silica gel employing a SIMS/Biotage Flash chromatography system and a 7% solution of methanol in methylene chloride as the eluent to yield the title compound in free base form as a white crystalline solid (melting point 138° C.–140° C., $^{13}$CNMR (ppm)=119.59).

Alternatively, the reaction may be carried out using tetrahydrofuran as solvent instead of methylene chloride; furthermore, the chromatography step may be eliminated.

EXAMPLES 2 TO 12

The following compounds are prepared analogous to the method of Example 1 (especially Step C):

| Example | Structure | M.P. [° C.] |
| --- | --- | --- |
| 2 | Pyrrolidine, 1-[[(3,5-dimethyl-1-adamantyl)amino]-acetyl]-2-cyano-, (S)- | 103–105 (HCl) |
| 3 | Pyrrolidine, 1-[[(3-ethyl-1-adamantyl)amino]acetyl]-2-oyano-, (S)- | 212–214 (HCl) |
| 4 | Pyrrolidine, 1-[[(3-methoxy-1-adamantyl)amino]-acetyl]-2-cyano-, (S)- | 92–94 (HCl) |
| 5 | Pyrrolidine, 1-[[[3-[[(t-butylamino)carbonyl]oxy]-1-adamantyl]amino]acetyl]-2-cyano-, (S)- | 210–212 (HCl) |

-continued

| Example | Structure | M.P. [° C.] |
|---|---|---|
| 6 | Pyrrolidine, 1-[[[3-[[[(4-methoxyphenyl)amino]-carbonyl]oxy]-1-adamantyl]amino]acetyl]-2-cyano-, (S)- | 212–214 (HCl) |
| 7 | Pyrrolidine, 1-[[[3-[[(phenylamino)carbonyl]oxy]-1-adamantyl]amino]acetyl]-2-cyano-, (S)- | 205–207 (HCl) |
| 8 | Pyrrolidine, 1-[[(5-hydroxy-2-adamantyl)amino]-acetyl]-2-cyano-, (S)- | [$^{13}$C NMR (CN group): 121.56 (ppm)] (HCl) |
| 9 | Pyrrolidine, 1-[[(3-acetyloxy-1-adamantyl)amino]-acetyl]-2-cyano-, (S)- | [$^{13}$C NMR (CN group): 118.54 (ppm)] |

-continued

| Example | Structure | M.P. [° C.] |
|---------|-----------|-------------|
| 10 | Pyrrolidine, 1-[[[3-[[[(diisopropyl)amino]carbonyl]-oxy]-1-adamantyl]amino]acetyl]-2-cyano-, (S)- | 148–150 (HCl) |
| 11 | Pyrrolidine, 1-[[[3-[[[(cyclohexyl)amino]carbonyl]-oxy]-1-adamantyl]amino]acetyl]-2-cyano-, (S)- | 155–157 (HCl) |
| 12 | Pyrrolidine, 1-[[(3-ethoxy-1-adamantyl)amino]-acetyl]-2-cyano-, (S)- | [$^{13}$C NMR (CN group): 119.31 (ppm)] (HCl) |

(HCl) = as hydrochloride

All HCl salts of final products are prepared by passing HCl gas through a 0.1 Molar solution of the free base in tetrahydrofuran until solution is clearly acidic followed by removal of the solvent (rotovap/pump).

The amino-adamantane starting materials are known in the literature or can be prepared as follows:

The manufacture of 3,5-dimethyl-1-adamantylamine is described in J. Med. Chem, 25; 1; 1982; 51–56.

The manufacture of 3-ethyl-1-adamantylamine is described in J. Med. Chem, 25; 1; 1982; 51–56.

3-Methoxy-1-adamantylamine can be prepared as follows

To a stirred, ice-water chilled suspension of potassium hydride (0.680 gm; 5.95 mmol) in 15.0 ml of tetrahydofuran is added a mixture of 1-aminoadamantane-3-ol (1.00 g; 5.95 mmol) and 15.0 ml of tetrahydrofuran dropwise over 30 minutes. The resulting mixture is then stirred for an addition 30 minutes and iodomethane (0.370 ml; 5.95 mmol) is then added dropwise over one minute. The resulting opaque white reaction is then stirred at room temperature for 18 hours. The mixture is then diluted with 50 ml of methylene chloride and filtered to remove the inorganic impurities. The filtrate is then concentrated and purified on silica gel employing a SIMS/Biotage apparatus and 19% methanol and 19% ammonium hydroxide in methylene chloride as eluent to yield 3-methoxy-1-adamantylamine as an opaque oil.

Synthesis of 3-[[(tertbutylamino)carbonyl]oxy]-1-aminoadamantane

To a mixture of 1-aminoadamantane-3-ol (5.00 g; 30.0 mmol) and potassium carbonate (6.20 g; 45 mmol) in 150 ml of tetrahydrofuran is added benzylchloroformate (4.70 g, 33.0 mmol) in dropwise fashion over a 10 minute period. The mixture is then stirred at room temperature for 2 h and then partitioned between ethyl acetate and water. The product is then extracted into the ethyl acetate and the aqueous layer is washed twice with ethyl acetate (100 ml). The combined organic layers are then washed successively with 100 ml of aqueous 2 N sodium hydroxide, water and brine, dried over sodium sulfate, filtered and concentrated (rotovap/pump) to provide 1-benzylcarbamoyladamantane-3-ol as a white solid in 85% yield.

To a clear solution of 1-benzylcarbamoyladamantane-3-ol (1.00 g: 3.32 mmol) and tert-butylisocyanate (380 µl, 3.32 mmol) in 30 ml of methylene chloride is syringe-added trimethylsilyl chloride (20.0 μl, 0.17 mmol). This reaction is then stirred at room temperature for 18 hours, concentrated (rotovap) and purified on silica gel employing a SIMS/Biotage apparatus and 20% ethyl acetate in hexane as eluent to yield 3-[[(tertbutylamino)carbonyl]oxy]-1-benzylcarbamoyladamantane as a white solid in quantitative yield.

To a mixture of 3-[[(tertbutylamino)carbonyl]oxy]-1-benzylcarbamoyladamantane (1.50 g, 3.75 mmol) and 10% palladium on carbon (400 mg) in ethanol (150 ml) in a 1-liter parr hydrogenation flask is added hydrogen (50 psi). This opaque black mixture is then shaken for 24 h. The reaction is then filtered through celite to remove the palladium catalyst and concentrated (rotovap/pump) to provide 3-[[(tertbutylamino)carbonyl]oxy]-1-aminoadamantane as a clear oil in 99% yield.

The procedure for the synthesis of 4-[[[(methoxyphenyl) amino]carbonyl]oxy]-1-aminoadamantane is essentially the procedure of 3-[[(tertbutylamino)carbonyl]oxy]-1-aminoadamantane except in the second step where an equivalent of 4-methoxyphenyl isocyanate replaces tert-butylisocyanate, 1,2-dichloroethane is used as solvent instead of methylene chloride and the reaction is stirred at 50° C. for 18 hours. The final amine intermediate is provided as an oil.

The procedure for the synthesis of 3-[[(phenylamino) carbonyl]oxyl]-1-aminoadamantane is essentially the procedure of 3-[[(tertbutylamino)carbonyl]oxy]-1-aminoadamantane except in the second step where an equivalent of phenyl isocyanate replaces the tert-butylisocyanate, 1,2-dichloroethane is used as solvent instead of methylene chloride and the reaction is stirred at 50° C. for 18 hours. The final amine intermediate is provided as a clear oil.

The procedure to make 2-aminoadamantane-5-ol is the same as in Example 1 except that the starting material is 2-aminoadamantane instead of 1-aminoadamantane.

The procedure for the synthesis of the nucleophile 3-acetoxy-1-aminoadamantane is essentially the procedure of 3-[[(tertbutylamino)carbonyl]oxy]-1-aminoadamantane except for a standard acylation of 1-benzylcarbamoyladamantane-3-ol using 1.2 eq of acetyl chloride, 3.0 eq. of pyridine, 0.1 eq of 4-dimethylaminopyridine and 1,2 dichloroethane which are all stirred at room temperature for 24 hours. The final amine is provided as a thick oil.

The procedure for the synthesis of 3-[[[(diisopropyl) amino]carbonyl]oxy]-1-amino-adamantane is essentially the procedure of 3-[[(tertbutylamino)carbonyl]oxy]-1-aminoadamantane except in the second step where an equivalent of diisopropylcarbamoyl chloride replaces the tert-butylisocyanate, 1,2-dichloroethane is used as solvent instead of methylene chloride and the reaction is stirred at 85° C. for 18 hours. The final amine intermediate is provided as a gray solid.

The procedure for the synthesis of 3-[[[(cyclohexyl) amino]carbonyl]oxy]-1-aminoadamantane is essentially the procedure of 3-[[(tertbutylamino)carbonyl]oxy]-1-aminoadamantane except in the second step where an equivalent of cyclohexylisocyanate replaces the tert-butylisocyanate, 1,2-dichloroethane is used as solvent instead of methylene chloride and the reaction is stirred at 50° C. for 18 hours. The final amine intermediate is provided as a thick clear oil.

The procedure to make 3-ethoxy-1-adamantylamine (a clear oil) is the same as for 3-methoxy-1-adamantylamine except that iodoethane (1.3 equivalent) is used instead of iodomethane.

Formulation Example

Tablets, each containing 50 mg of active ingredient, for example, (S) 1[[(3-hydroxy-1-adamantyl)amino]acetyl-2-cyano-pyrrolidine, can be prepared as follows:

| Composition (for 10,000 tablets) | |
|---|---|
| Active ingredient | 500.0 g |
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened using an alcoholic solution of the gelatin and granulated by means of a sieve. After drying, the remainder of the potato starch, the talc, the magnesium stearate and the highly disperse silica are admixed and the mixture is compressed to give tablets of weight 145.0 mg each and active ingredient content 50.0 mg which, if desired, can be provided with breaking notches for finer adjustment of the dose.

What is claimed is:

1. A compound of formula I:

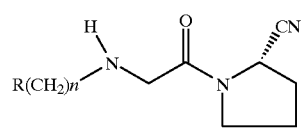

wherein

R is substituted adamantyl; and n is 0 to 3; in free form or in acid addition salt form.

2. A compound according to claim 1 of formula (I A) or (I B)

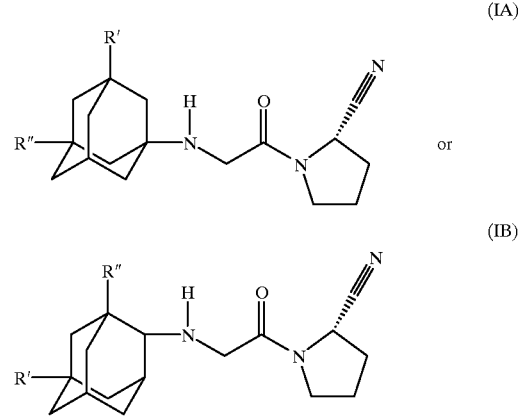

wherein R' represents hydroxy, $C_1$–$C_7$alkoxy, $C_1$–$C_8$-alkanoyloxy, or $R_5R_4N$—CO—O——, where $R_4$ and $R_5$ independently are $C_1$–$C_7$alkyl or phenyl which is unsubstituted or substituted by a substituent selected from $C_1$–$C_7$alkyl, $C_1$–$C_7$alkoxy, halogen and trifluoromethyl and where $R_4$ additionally is hydrogen; or $R_4$ and $R_5$ together represent $C_3$–$C_6$alkylene; and R" represents hydrogen; or R' and R" independently represent $C_1$–$C_7$alkyl; in free form or in form of a pharmaceutically acceptable acid addition salt.

3. A compound according to claim 1 selected from the group consisting of:

pyrrolidine, 1-[[(3,5-dimethyl-1-adamantyl)amino]-acetyl]-2-cyano-, (S)-;

pyrrolidine, 1-[[(3-ethyl-1-adamantyl)amino]acetyl]-2-cyano-, (S)-;

pyrrolidine, 1-[[(3-methoxy-1-adamantyl)amino]-acetyl]-2-cyano-, (S)-;

pyrrolidine, 1-[[[3-[[(t-butylamino)carbonyl]oxy]-1-adamantyl]amino]acetyl]-2-cyano-, (S)-;

pyrrolidine, 1-[[[3-[[[(4-methoxyphenyl)amino]-carbonyl]oxy]-1-adamantyl]amino]acetyl]-2-cyano-, (S)-;

pyrrolidine, 1-[[[3-[[(phenylamino)carbonyl]oxy]-1-adamantyl]amino]acetyl]-2-cyano-, (S)-;

pyrrolidine, 1-[[(5-hydroxy-2-adamantyl)amino]-acetyl]-2-cyano-, (S)-;

pyrrolidine, 1-[[(3-acetyloxy-1-adamantyl)amino]acetyl]-2-cyano-, (S)-;

pyrrolidine, 1-[[[3-[[[(diisopropyl)amino]carbonyl]oxy]-1-adamantyl]amino]acetyl]-2-cyano-, (S)- pyrrolidine, 1-[[[3-[[[(cyclohexyl)amino]carbonyl]oxy]-1-adamantyl]amino]acetyl]-2-cyano-, (S)-; and pyrrolidine, 1-[[(3-ethoxy-1-adamantyl)amino]acetyl]-2-cyano-, (S)-;

or, in each case, a pharmaceutically acceptable acid addition salt thereof.

4. A compound according to claim 1 which is pyrrolidine, 1-[(3-hydroxy-1-adamantyl)amino]acetyl-2cyano-, (S), or a pharmaceutically acceptable acid addition salt thereof.

5. A pharmaceutical composition comprising a compound according to claim 1 in free form or in pharmaceutically acceptable acid addition salt form, together with at least one pharmaceutically acceptable carrier or diluent.

6. A method of inhibiting dipeptidyl peptidase-IV comprising administering to a mammal in need of such treatment a therapeutically effective amount of a compound according to claim 1, or a pharmaceutically acceptable acid addition salt thereof.

7. A method of treating conditions mediated by dipeptidyl peptidase-IV inhibition comprising administering to a mammal in need of such treatment a therapeutically effective amount of a compound according to claim 1, or a pharmaceutically acceptable acid addition salt thereof.

8. The method according to claim 7 wherein the condition treated is non-insulin-dependent diabetes mellitus.

9. The method according to claim 7 wherein the condition treated is obesity.

* * * * *

UNITED STATES PATENT AND TRADEMARK OFFICE
CERTIFICATE OF CORRECTION

PATENT NO.    : 6,166,063
DATED         : December 26, 2000
INVENTOR(S)   : Edwin Bernard Villhauer Page 1 of 2

It is certified that error appears in the above-identified patent and that said Letters Patent is hereby corrected as shown below:

Title page,
Item [63] should read:
-- [60] Provisional Application No. 60/219,313, Dec. 10, 1998. --

Column 1,
Lines 7-9 should read:
-- This application claims the benefit of U.S. Provisional Application No. 60/219,303, filed Dec. 10, 1998, which was converted from U.S. Application No. 09/209,068, and which is incorporated herein by reference. --

Column 2,
Line 11, delete "the".
Line 13, delete the second occurrence of "the".

Column 8,
Line 3, change "a" to -- are --.

Column 10, Example 3,
Line 2, beneath the structural formula, change "2-oyano" to -- 2-cyano --.

Column 11, Example 6,
Structural formula should read:

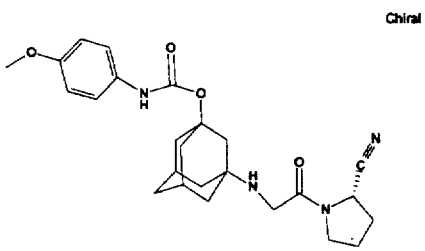

UNITED STATES PATENT AND TRADEMARK OFFICE
CERTIFICATE OF CORRECTION

PATENT NO. : 6,166,063
DATED : December 26, 2000
INVENTOR(S) : Edwin Bernard Villhauer Page 2 of 2

It is certified that error appears in the above-identified patent and that said Letters Patent is hereby corrected as shown below:

Column 11, Example 7,
Structural formula should read:

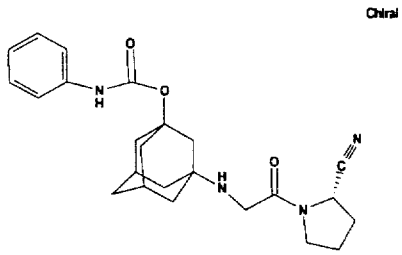

Column 14,
Line 47, change "19%" to -- 1% --.

Column 16,
Line 4, after the first occurrence of "1", insert a hyphen.

Column 18,
Line 6, after "2", insert a hyphen.

Signed and Sealed this

Sixth Day of November, 2001

*Attest:*

*Attesting Officer*

NICHOLAS P. GODICI
*Acting Director of the United States Patent and Trademark Office*